US005434069A

United States Patent [19]

Tsaur et al.

[11] Patent Number: 5,434,069

[45] Date of Patent: Jul. 18, 1995

[54] CAPSULE COMPRISING OIL SURROUNDING HYDROPHOBIC OR HYDROPHILIC ACTIVE AND POLYMERIC SHELL SURROUNDING OIL

[75] Inventors: Liang S. Tsaur, Norwood; Shiji Shen, River Edge, both of N.J.; Michael P. Aronson, West Nyack, N.Y.; David J. Pocalyko, Lincoln Park, N.J.

[73] Assignee: Lever Brothers Company, Division of Conopco, Inc., New York, N.Y.

[21] Appl. No.: 150,701

[22] Filed: Nov. 12, 1993

[51] Int. Cl.$^6$ .......................... C12N 9/96; C11D 17/08

[52] U.S. Cl. .................................... 435/188; 252/79.1; 252/99; 252/100; 252/102; 252/104; 252/174.12; 252/174.13; 252/174.23; 435/182; 435/264; 435/281; 428/402.2; 428/402.21; 428/402.22

[58] Field of Search ............... 435/264, 281, 182, 188; 252/174.12, 174.13, 79.1, 102, 100, 99, 104, 174.23; 428/402.22, 402.2, 402.21

[56] References Cited

U.S. PATENT DOCUMENTS

| | | | |
|---|---|---|---|
| 4,098,736 | 7/1978 | Li et al. | 428/402.2 |
| 4,777,089 | 10/1988 | Takizawa et al. . | |
| 4,906,396 | 3/1990 | Falholt et al. | 252/174.12 |
| 4,919,841 | 4/1990 | Kamel et al. | 428/402.2 |
| 5,013,473 | 5/1991 | Norbury et al. | 252/174.13 |
| 5,047,163 | 9/1991 | Batal et al. . | |
| 5,318,728 | 6/1994 | Surutzidis et al. | 252/548 |
| 5,324,445 | 6/1994 | Langley et al. | 252/174.12 |
| 5,385,959 | 1/1995 | Tsaur et al. | 428/402.24 |

FOREIGN PATENT DOCUMENTS

| | | |
|---|---|---|
| 0266796 | 5/1988 | European Pat. Off. . |
| 0356239 | 2/1990 | European Pat. Off. . |
| 273775 | 11/1992 | European Pat. Off. . |
| 1390503 | 4/1975 | United Kingdom . |
| 90/14336 | 11/1990 | WIPO . |
| 92/20771 | 11/1992 | WIPO . |

*Primary Examiner*—Herbert J. Lilling
*Attorney, Agent, or Firm*—Ronald A. Koatz

[57] ABSTRACT

The present invention relates to a novel capsule for protecting sensitive ingredients in detergent compositions. The capsule, in addition to a protected sensitive ingredient, contains an oil dispersion containing the active and a polymer shell surrounding the dispersion. The oil is defined by its ability to meet a tripartite definition and the shell is a water soluble or water dispersible polymer as defined.

8 Claims, No Drawings

CAPSULE COMPRISING OIL SURROUNDING HYDROPHOBIC OR HYDROPHILIC ACTIVE AND POLYMERIC SHELL SURROUNDING OIL

BACKGROUND OF THE INVENTION

1. Field of the Invention

The present invention relates to a novel capsule capable of protecting sensitive active ingredients (e.g., enzymes, peracid bleaches or bleach catalysts)in liquid detergent compositions.

2. Background

It is well known in the ad that liquid detergents may provide a hostile environment to sensitive ingredients (e.g., enzymes, peracid bleach, bleach catalysts or perfumes) used in these detergents. For example, enzymes are subject to attack by, anionic actives, high pH conditions and/or by other enzymes. Bleaches, in particular peracid bleaches (such as taught in U.S. Pat. No. 4,909,953 and WO/90, 14,336, for example), are known to be particularly harsh on enzyme components. Encapsulation has been used to protect these sensitive ingredients in liquid detergent.

One approach to protecting these sensitive ingredients is to in fact use a polymer shell surrounding the active component to protect the component. This approach has been used, for example, in GB 1,390,503 to Unilever; in EP 266,796 to Showa Denko; and in U.S. Pat. No. 4,777,089 (Lion Corp.).

While such an approach has been effective in protecting active components such as enzyme or enzymes from being attacked by other enzymes or harsh surfactants, this type of capsule does not provide an effective barrier to protect the component from being attacked by bleach. Bleach molecules can penetrate rapidly through the polymer coating and interact with the sensitive ingredient.

In copending patent applications U.S. Ser. Nos. 07/875,872 and 07/875,914, applicants teach an encapsulating polymer system comprising a hydrophilic water soluble polymer or polymers chemically or physically attached to a hydrophobic polymer core particles. Although these applications teach a kind of "web-like" capsule created by the hydrophilic molecules entangling and forming an encapsulating net over the core, this "net" is still too porous to protect the active component, particularly when the liquid composition is a bleach containing liquid composition Another method which has been used to protect active components from the liquid medium is to place the active in a hydrophobic oil such that the active is protected by the oil from diffusing into the composition where it is subject to degradative attack.

Each of U.S. Pat. No. 4,906,396 to Falholt et al.; EP 356,239 to Allied Colloid; and EP 273,775, for example, provide enzymes protected by hydrophobic oils.

The use of a hydrophobic oil alone, however, does not provide sufficient protection, particularly when the composition also contains powerful degradative components such as the peracid bleaches mentioned above. This may be because the hydrophobic oils were simply not selected carefully enough to deter migration of the degradative components toward the active or, conversely, migration of the active toward the degradative component.

U.S. Pat. No. 4,906,396 to Falholt et al. discloses a detergent enzyme dispersed in a hydrophobic oil. As seen in the examples which follow, the hydrophobic oil is simply incapable of slowing degradation of the enzyme, for example, when placed in a bleach containing liquid composition. Again, whether this is because the hydrophobic oil was not properly selected to sufficiently slow migration of enzyme to bleach or visa versa is unknown. However, the hydrophobic oil alone simply does not function effectively such as the capsules of the subject invention.

In WO 92/20771, Allied Colloids Limited teaches a particulate composition comprising particles having a substantially anhydrous core comprising a matrix polymer containing active ingredient, a layer of hydrophobic oil around the core and a polymer shell around the oil. It is said that the matrix polymer (which contains the active) should be sufficiently hydrophobic that it will partition into the oil rather than the water.

The problem addressed by the patent is that, without the hydrophobic matrix polymer, the active migrates out of the oil too quickly and won't stay in the oil. In other words, the oil layer is incapable of holding a hydrophilic particle without the hydrophobic matrix polymer. Although the retention of a hydrophilic active ingredient by the oil can be enhanced by entrapping the active ingredient with a hydrophobic matrix polymer, this requires modifying the active ingredient with hydrophobic matrix polymer before making the capsule. This in turn both is costly and causes the problem of not rapidly and efficiently releasing the active ingredient in use.

The subject invention differs from the reference in that the oil layer of the subject invention is selected such that it can retain a hydrophilic active in the absence of matrix polymer. Further, as noted above, since the active is not associated with a hydrophobic matrix polymer, it is more readily and efficiently released in use (e.g., when the polymer shell is dissolved).

Accordingly, there is a need in the art for some kind of capsule composition which more effectively protects active ingredients, particularly hydrophilic ingredients, from bleaches or other harsh components found in the detergent composition.

Further, there is a need to find such a capsule which also readily and efficiently releases the actives in use, e.g., when the polymeric shell is dissolved or disintegrated.

SUMMARY OF THE INVENTION

The present invention provides a novel capsule system which protects actives in detergent compositions (i.e., particularly bleach containing compositions) and which effectively releases the actives in use wherein said capsule system comprises: (1) an oil dispersion containing the active and in which the oil is selected by meeting certain defined criteria; and (2) an outer polymer shell surrounding the oil dispersion.

DETAILED DESCRIPTION OF THE INVENTION

The present invention relates to a novel capsule system which protects actives in detergent compositions and also rapidly and efficiently releases the encapsulated active in use.

The capsule system is in effect a combination of (1) an oil dispersion which holds the actives in place and both keeps the actives from diffusing into solution and also provides a barrier preventing bleach or other harsh factors/components (anionics or pH conditions) from coming into contact with the active; and (2) an outer polymer shell surrounding the oil dispersion to prevent the deformation of the oil dispersion during and after addition to the liquid detergent.

The oil in component (1) is selected by meeting a combination of defined criteria as set forth in greater detail below.

Oil Component

The first component of the capsule system is the hydrophobic oil component.

The oil components of the invention are defined by meeting each of three defined criteria set forth below: (1) by their ability to retain active in the dispersion in an aqueous solution; (2) by their ability to withstand phase separation at ambient or elevated temperatures over time; and (3) by their ability to rapidly and effectively release the encapsulated active in use. As noted, the oils must meet all three defined criteria to be selected as the oil component of the invention.

According to the first criteria, the oil component is defined by its ability to retain at least 80% active, preferably 90% after adding the active in oil dispersion to an aqueous solution containing 0.5 wt. % of surfactant for an hour without mixing. Testing was done using sodium lauryl sulfate although any suitable surfactant may be used.

A second criteria by which the oil component is defined is its ability to hold the active in place and to prevent the active from diffusing or precipitating out of the oil phase. The stability of active in oil dispersion can be determined by adding the active in oil dispersion to a 10 ml graduated cylinder and measuring the phase separation of the active from the hydrophobic oil. It should be less than 10%, preferably less than 5% of phase separation when measured at 37° C. for 1 week.

The last criteria used to define the oil component is its ability to rapidly and effectively release the active in use. The oil release property can be determined by a standard Terg-O-Meter washing method. Terg-O-Meter are well known in the art such as, for example Terg-O-Tometer UR7227. In these devices, generally, 500 mls of wash liquid are agitated at above 70 rpm for about 20 minutes using desired wash liquid. The capsules of the invention were tested using 1000 mls at 100 rpm for 15 minutes at 40° C.

The capsule should release more than 50%, preferably more than 70% of the active after the first five minutes of the wash cycle when measured at 40° C.

The hydrophobic oil component can be a liquid or a semisolid at room temperature. Liquid oils alone with a viscosity of less than 10,000 centipoises (cps) such as mineral oils, silicone oils or vegetable oils are not suitable for this invention and require modification. These oils do not have the capability to hold and retain hydrophilic actives and do not provide a sufficient protection to the active in a liquid detergent. The preferred liquid oil components are oils containing hydrophobic particles with particle size less than 3μ, preferably less than 1μ, more preferably less than 0.1μ. Examples of such hydrophobic particles are hydrophobic silica such as Cabot's Cab-O-Sil TS 720 and Cab-O-Sil TS 530 or Degussa's Aerosil 200; and hydrophobic clay such as Rheox's Bentone SD-1. These hydrophobic particles can be incorporated into the oil physically i.e., simply by mixing the oil with the hydrophobic particles or chemically, i.e., through the chemical interaction of oil with the surface of the particles. The preferred hydrophobic particles are submicron sized hydrophobically modified fumed silica such as Cab-O-Sil TS 720. These hydrophobic particles can enhance the suspension of active in the oil and also increase the capability of oil to retain the active in an aqueous solution. Typically the amount of hydrophobic particles in the oil is less than 15%, preferably less than 10%, more preferably less than 5% but more than 0.5% should be used.

In preferred embodiments of the invention, the oil component is defined by the fact that it is a semisolid rather than a liquid at room temperature. Specifically, when the component has a melting temperature of from about 35° C. to 70° C., preferably 40° C. to 65° C., the semisolids are found to retain the active more readily. Moreover, such materials release active under wash condition rapidly enough to give wash performances comparable to compositions in which enzymes have been newly added. Since these semisolid oils will also slow migration of active out of the oil phase or slow migration of bleach and other harsh components toward the active, they are again preferred.

Examples of such semisolid oils are petrolatums such as Penreco's Penreco Snow, Mineral Jelly and Tro-Grees; Witco's Multiwax; and fats (e.g., glyceryl ester of $C_{12}$–$C_{24}$ fatty acids) or fat derivatives such as mono-, di- or tri-glycerides and fatty alkyl phosphate ester. Hydrophobic particles such as hydrophobic fumed silica are also desirably incorporated into these semisolid oils to further enhance their ability to retain actives, especially when the capsule of this invention is processed or stored at a temperature close to or above the melting point of the semisolid oils.

The oil around the active will generally comprise about 98% to 40%, preferably 90% to 70% of the active in oil dispersion.

Polymer Coating

The second component of the capsule system is the polymer coating surrounding the active in oil dispersion.

The polymer suitable for this invention must be insoluble in the composition of the liquid cleaning product and must disintegrate or dissolve during the use of the product simply by dilution with water, pH change or mechanical forces such as agitation or abrasion. The preferred polymers are water soluble or water dispersible polymers that are or can be made insoluble in the liquid detergent composition. Such polymers are described in EP 1,390,503; U.S. Pat. No. 4,777,089; U.S. Pat. No. 4,898,781; U.S. Pat. No. 4,908,233; U.S. Pat. No. 5,064,650 and U.S. Ser. Nos. 07/875,872 and 07/875,194, all of which are incorporated by reference into the subject application.

These water soluble polymers display an upper consulate temperature or cloud point. As is well known in the art (P. Molyneaux, Water Soluble Polymers CRC Press, Boca Raton, 1984), the solubility or cloud point of such polymers is sensitive to electrolyte and can be "salted out" by the appropriate type and level of electrolyte. Such polymers can generally be efficiently salted out by realistic levels of electrolyte (<10%). Suitable polymers in this class are synthetic nonionic water soluble polymers including: polyvinyl alcohol; polyvinyl pyrrolidone and its various copolymers with styrene and vinyl acetate; and polyacrylamide and its vadous modification such as those discussed by Molyneaux (see above) and McCormick (in Encyclopedia of Polymer Science Vol 17, John Wiley, New York). Another class of useful polymers are modified polysaccharides such as carrageenan, guar gum, pectin, xanthan gum, partially hydrolyzed cellulose acetate, hydroxy ethyl, hydroxy propyl and hydroxybutyl cellulose, methyl cellulose and the like. Proteins and modified proteins such as gelatin are still another class of polymers useful in the present invention especially when selected to have an isoelectric pH close to that of the liquid composition in which the polymers are to be employed.

From the discussion above, it is clear that a variety of hydrophilic polymers have potential utility as the polymer coating for the capsules of this invention. The key is to select an appropriate hydrophilic polymer that would be essentially insoluble in the composition (preferably a concentrated liquid system) under the prevailing electrolyte concentration, yet would dissolve or disintegrate when this composition is under conditions of use. The tailoring of such polar polymers is well within the scope of those skilled in the art once the general requirements are known and the principle set forth.

Capsule

The capsule of this invention can be produced by a variety of known encapsulation processes. For example, the capsule can be prepared according to the coacervation process in which the active in oil dispersion is dispersed to an aqueous solution of a water soluble or water dispersible polymer. In this procedure, a non-solvent for the polymer or an electrolyte is added or a pH change or a pressure change is effected to make the capsule. Examples of this coacervation process are described in U.S. Pat. No. 4,777,089, U.S. Pat. No. 3,943,063 and U.S. Pat. No. 4,978,483, all three of which are incorporated herein by reference. Similarly, the capsule can be formed by adding the emulsion of active in oil in polymer solution to the nonsolvent. In this process, the oil composition and the emulsification process are critical because the active must stay within the oil rather than diffuse out during the emulsification of the active in oil dispersion to a polymer solution. Hydrophobic particles, especially submicron fumed silica, are especially useful to help the retention of actives in the oil during emulsification. The oil should contain a sufficient amount of the hydrophobic particles to prevent the diffusion of the hydrophilic active out of oil. The amount of hydrophobic particles in the oil is greater than 0.5%, preferably greater than 3% and less than 10%. The emulsification process should be carried out in a mild condition to prevent overmixing of the active in oil dispersion with the polymer solution and to ensure the resulting oil droplet size is larger than the particle size of the active.

The capsule of the invention also can be prepared by extrusion nozzles as taught in U.S. Pat. No. 3,310,612, U.S. Pat. No. 3,389,194 or U.S. Pat. No. 2,799,897 and GB 1,390,503. In these processes, the active in oil dispersion is extruded through the inert orifice of the nozzle. Simultaneously, the water soluble polymer solution is extruded through the outer orifice of the nozzle to form a uniform coating on the surface of active in oil dispersion. The capsule is then formed by breaking the coextrudate at the end of the nozzle orifice by air, centrifuge force, blade or carry fluid to form droplets which are hardened in a nonsolvent of the water-soluble polymer to form the capsule.

Active

The active materials which are desired to be encapsulated by the capsule of this invention are those materials which will lose their activity in a cleaning product, especially a bleach-containing liquid cleaning product, if no hydrophobic oil coating is added according to this invention. The active materials protected by the oil layer may be a hydrophilic active (e.g., enzyme or bleach catalyst) or a hydrophobic active (e.g., perfume) and can be solid, liquid or in aqueous solution. If it is a solid material, the particle size of the active should be less than 200μ preferably less than 501μ. Of course, since a hydrophobic active is generally readily protected by an oily layer and is generally not readily degraded by harsh components in composition, the benefits of the invention are more readily apparent when the active ingredient is a hydrophilic one. Hydrophilic actave materials include enzymes, bleach catalysts peracid bleaches, bleach activators and optical brighteners.

One preferred ingredient of the capsules disclosed herein is an enzyme. The enzymes may be amylases, proteases, lipases, oxidases, cellulases or mixtures thereof. The amylolytic enzymes for use in the present invention can be those derived from bacteria or fungi. Preferred amylolytic enzymes are those described in British Patent Specification No. 1,296,839, cultivated from the strains of *Bacillus licheniformis* NCIB 8061, NCIB 8059, ATCC 6334, ATCC 6598, ATCC 11,945, ATCC 8480 and ATCC 9945A. A particularly preferred enzyme is an amyiolytic enzyme produced and distributed under the trade name, Termamyl, by Novo Industri A/S, Copenhagen, Denmark. These amylolytic enzymes are generally sold as granules and may have activities from about 2 to 10 Maltose units/milligram. The amylolytic enzyme is normally included in an amount of from 1% to 40% by weight of the capsule, in particular from 5 to 20% by weight.

The active may also be a proteolytic enzyme. Examples of suitable proteolytic enzymes are the subtilisins which are obtained from particular strains of *B. subfills* and *B. licheniformis,* such as those commercially available under the trade names Maxatase, supplied by Gist-Brocades NV, Delft, Netherlands, and Alcalase, supplied by Novo Industri NS, Copenhagen, Denmark. Particularly preferred are the proteases obtained from a strain of Badflus having a maximal activity throughout the pH range of 8–12, being commercially available under the trade names of Esperase and Savinase, sold by Novo Industri A/S. These proteolytic enzymes are generally sold as granules and may have enzyme activities of from about 500 to 50,000 glycine units/milligram. The proteolytic enzyme is normally included in an amount of from about 1% to about 40% by weight of the capsule, in particular of from 5% to 20% by weight.

Lipolytic enzymes may also be included in order to improve removal of fatty soils. The lipolytic enzymes are preferably included in an amount of from about 1% to about 40%, preferably from 5% to 20% by weight. Cellulase enzymes may be used in an amount from about 1% to 40% by weight of the capsule.

The total content of the enzyme in the capsules of the present invention is from about 1% to about 40%, preferably from about 5% to about 20%.

It should be understood that the enzyme may also be a genetically engineered variation of any of the enzymes described have engineered to have a trait (e.g., stability) superior to its natural counterpart.

The protected active may also be peroxygen compound activators, peracid bleaches, bleach catalysts, optical brighteners or perfumes.

Peroxygen compound activators are organic compounds which react with the peroxygen salts (e.g. sodium perborate, percarbonate, persilicate) in solution to form an organic peroxygen acid as the effective bleaching agent. Preferred activators include tetraacetylethylenediamine, tetraacetylglycoluril, glucosepentaacetate, xylose tetraacetate, sodium benzoyloxybenzene sulfonate and choline sulfophenyl carbonate. The activators may be released from the capsule to combine with peroxygen compound in the composition.

When activator is included, the ratio between the peroxygen in solution and the activator lies in the range of from 8:1 to 1:3, preferably 4:1 to 1:2, and most preferably is 2:1.

Although peroxyacids are generally contemplated for use in the composition rather than the capsule, peroxyacid compounds may be used as the active in the capsule as well, particularly in compositions where conditions are so harsh as to deactivate the peroxyacid.

Generally the peroxyacids are amido or imido peroxyacids and are present in the range from about 0.5 to about 50%, preferably from about 15 to about 30% by weight of the capsule. Preferably, the peroxyacid is an amide peracid, More preferably, the amide is selected from the group of amido peracids consisting of N,N'-Terephthaloyl-di(6-aminopercarboxycaproic acid) (TPCAP), N,N'-Di(4-percarboxybenzoyl)piperazine (PCBPIP), N,N'-Di(4-Percarboxybenzoyl)ethylenediamine (PCBED), N,N'-di(4-percarboxybenzoyl)-1,4-butanediamine (PCBBD), N,N'-Di(4-Percarboxyaniline)terephthalate (DPCAT), N,N'-Di(4-Percarboxybenzoyl)-1,4-diaminocyclohexane (PCBHEX), N,N'-Terephthaloyl-di(4-amino peroxybutanoic acid) ($C_3$ TPCAP analogue called TPBUTY) N,N'-Terphthaloyl-di(8-amino peroxyoctanoic acid) ($C_7$ TPCAP analogue called TPOCT), N,N'-Di(percarboxyadipoyl)phenylenediamine (DPAPD) and N,N'-Succinoyl-di(4percarboxy)aniline (SDPCA). Such compounds are described in WO 90/14,336.

Other peroxyacids which may be used include the amidoperoxy acids disclosed in U.S. Pat. Nos. 4,909,953 to Sadowski and U.S. Pat. No. 5,055,210 to Getty, both of which are incorporated by reference into the subject application.

Also, the active inside the compounds may be a bleach catalyst (i.e. for activating peracids found in the composition outside the capsule).

Examples of such catalysts include manganese catalysts of the type described in U.S. Pat. No. 5,153,161 or U.S. Pat. No. 5,194,416, both of which are incorporated by reference into the subject application; sulfonomine catalysts and derivatives such as described in U.S. Pat. Nos. 5,041,232 to Batal, U.S. Pat. No. 5,045,223 to Batal and U.S. Pat. No. 5,047,163 to Batal, all three of which are incorporated by reference into the subject application.

More particularly, manganese catalysts include, for example, manganese complexes of the formula:

IV $[LMn(OR)_3]Y$ wherein

Mn is manganese in the +4 oxidation state;

R is a $C_1$–$C_{20}$ radical selected from the group consisting of alkyl, cycloalkyl, aryl, benzyl and radical combinations thereof;

at least two R radicals may also be connected to one another so as to form a bridging unit between two oxygens that coordinate with the manganese;

L is a ligand selected from a $C_3$–$C_{60}$ radical having at least 3 nitrogen atoms coordinating with the manganese; and Y is an oxidatively-stable counterior.

The sulfonomines include compounds having the structure:

$R^1R^2C=NSO_2R^3$ wherein:

$R^1$ may be a substituted or unsubstituted radical selected from the group consisting of hydrogen, phenyl, aryl, heterocyclic ring, alkyl and cycloalkyl radicals;

$R^2$ may be a substituted or unsubstituted radical selected from the group consisting of hydrogen, phenyl, aryl, heterocyclic ring, alkyl, cycloalkyl, $R^1C=NSO_2R^3$, nitro, halo, cyano, alkoxy, keto, carboxylic, and carboalkoxy radicals;

$R^3$ may be a substituted or unsubstituted radical selected from the group consisting of phenyl, aryl, heterocyclic ring, alkyl, cycloalkyl, nitro, halo and cyano radicals;

$R^1$ with $R^2$ and $R^2$ with $R^3$ may respectively together form a cycloalkyl, heterocyclic, and aromatic ring system.

Sulfonomine derivatives include compounds having the structure:

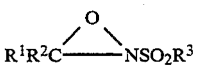

wherein:

$R^1$ may be a substituted or unsubstituted radical selected from the group consisting of hydrogen, phenyl, an/I, heterocyclic ring, alkyl and cycloalkyl radicals;

$R^2$ may be a substituted or unsubstituted radical selected from the group consisting of hydrogen, phenyl, aryl, heterocyclic ring, alkyl, cycloalkyl,

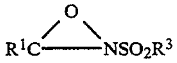

nitro, halo, cyano, alkoxy, keto, carboxylic and carboalkoxy radicals;

$R^3$ may be substituted or unsubstituted radical selected from the group consisting of phenyl, aryl, heterocyclic ring, alkyl, cycloalkyl, nitro halo, and cyano radicals;

$R^1$ with $R^2$ and $R^2$ with $R^3$ may respectively together form a cycloalkyl, heterocyclic, and aromatic ring system.

Bleach activators are particularly good candidates for bleach encapsulation both because they are used in very small amounts and because they are readily deactivated in solution.

More specifically, bleach activators are used in an amount from about 1% to 30% by weight of the capsule composition, preferably, 3% to 15% by weight.

As mentioned above, the actives may also be optical brighteners or perfumes.

Compositions

In a second embodiment of the invention, the invention relates to the use of the capsules in compositions, particularly aqueous detergent compositions. Preferably, the compositions are bleach containing aqueous detergent compositions. In fact, it is in those bleach containing aqueous detergent compositions that the benefits of the invention became readily apparent since it has previously been extremely difficult, if not impossible, to formulate capsules for use in bleach containing aqueous compositions wherein the actives are well protected in the capsule (e.g., greater than 80% active as defined above), yet readily release upon dilution.

The aqueous detergent compositions of the invention are typically structured (duotropic) or unstructured (isotropic) detergent compositions such as described in U.S. Pat. No. 5,089,163 to Aronson et al. or U.S. Pat. No. 4,908,150 to Hessel et al. (for isotropic liquids) or U.S. Pat. No. 4,992,194 to Liberati et al. or. U.S. Pat. No. 5,147,576 to Montague et al. (for structured liquids) all of which are incorporated by reference into the subject application.

Such compositions will generally comprise water, suffactants, electrolyte (for structuring and/or building purposes) and other ingredients such as are described below.

The surfactants may be anionic, nonionic, cationic, zwitterionic, or soap or mixtures thereof such as those described, for example, in U.S. Pat. No. 4,642,198 at columns 3 to 4.

The total surfactant amount in the liquid composition of the invention may vary from 2 to 60% by weight, preferably from 10 to 50% by weight, depending on the purpose of use. In the case of suspending liquids comprising an anionic and a nonionic surfactant the ratio thereof may vary from about 10:1 to 1:10. The term anionic surfactant used in this context includes the alkali metal soaps of synthetic or natural long-chain fatty acids having normally from 12 to 20 carbon atoms in the chain.

The total level of electrolyte(s) present in the composition to provide structuring may vary from about 1.5 to about 30%, preferably from 2.5 to 25% by weight.

In addition to the components discussed above, the heavy duty liquid detergent compositions of the invention may also contain certain optional ingredients in minor amounts. Typical examples of optional ingredients are suds-controlling agents, fluorescers, perfumes, coloring agents, abrasives, hydrotropes, sequestering agents, enzymes, and the like in varying amount.

Bleaches used in the invention may be any of those described in U.S. Pat. No. 4,992,194 to Liberati, hereby incorporated by reference. Peroxygen salts include salts such as sodium perborate, tetrahydrate or monohydrate, percarbonate, persilicate, persulfate, dipersulfate and the like. Other peroxygen compounds include perphosphates, peroxide and perpolyphosphates. As indicted above, the peroxygen salts may be activated by activators which may be encapsulated actives.

The decoupling polymer is also as disclosed in U.S. Pat. No. 4,992,194 Liberati. The bleaches may also be any of the peracid bleaches described in the "actives" section (i.e., the mono- or di- percarboxylic amido or imido acids) or the amido peroxy acids disclosed in U.S. Pat. Nos. 4,409,953 and 5,055,210, incorporated by reference.

In a preferred embodiment of the invention, the composition is a peracid bleach containing composition and the capsule of the invention (first embodiment) protects the active (e.g., enzyme or bleach catalyst) from the action of the peracid bleach (and other harsh components) in the liquid compositions.

The following examples are intended to further illustrate and describe the invention and are not intended to limit the invention in any way.

EXAMPLES

Preparation of Capsule and Detergent Composition

The capsule of this invention was prepared as described below using an enzyme slurry available from NOVO.

One pad of a commercially available silicone enzyme slurry Savinase 16SL/SR (ex. Novo, $3.5\times10^6$ GU/g Savinase activity) was added to two pads of neutralized Acrysol ASE-95 (which is a carboxylic acid containing polyacrylate latex) aqueous solution (ex. Rohm & Haas, 1.5 wt. %, pH =7.3–8.0). The mixture was stirred with an overhead stirrer for 20 minutes to form an enzyme-in-oil-in-water emulsion. The emulsion was added and hardened in an acid bath (98% water and 2% conc. $H_2SO_4$) using a Micro Dropper (Thies Technology) to form a matrix enzyme capsule of about 1,000 micrometers with $2.4\times10^6$ GU/g enzyme activity. The capsule was hardened in the acid bath for 40 minutes and stored in glycerol for further use.

This capsule was incorporated into the liquid detergent formula having the composition shown in Table I below:

TABLE 1

| BASE FORMULA OF LIQUID DETERGENT | |
|---|---|
| Water | 24.8 |
| Sorbitol (70%) | 15.8 |
| Glycerol | 4.76 |
| Sodium Borate $10H_2O$ | 4.76 |
| Sodium Citrate $2H_2O$ | 9.52 |
| Narlex DC-1 (ex. National Starch & Chem.)* | 3.0 |
| 50% NAOH | 5.43 |
| DB100 (Dow Chem.) (Antifoam) | 0.1 |
| Alkyl Benzene Sulfonic Acid | 21.83 |
| Neodol 25-9 (Nonionic) | 10.0 |
| Total | 100.00 |

*Hydrophobically modified polyacrylic acid aqueous solution having a molecular weight of about 4,000. Similar polymers are taught in U.S. Pat. No. 5,147,576 to Montague et al. which is hereby incorporated by reference into the subject application.

*Hydrophobically modified polyacrylic acid aqueous solution having a molecular weight of about 4,000. Similar polymers are taught in U.S. Pat. No. 5,147,576 to Montague et al. which is hereby incorporated by reference into the subject application.

The composition additionally contained sufficient amount of the peracid SBPB to have 1000 ppm active oxygen and was stored at 37° C.

EXAMPLE 1

In order to show that the capsule prepared as described above was superior to silicone enzyme slurry alone (i.e., the non-encapsulated silicone enzyme slurry), applicants prepared the same silicone enzyme slurry according to the procedure set forth in U.S. Pat. No. 4,906,396 by mixing this same silicone enzyme slurry (Savinase 16SL/SR (ex. Novo)) in the detergent composition set forth in Table 1 above.

Applicants additionally compared the residual enzyme activity of the enzyme after 2 and 6 days both when the enzymes were unprotected (i.e., liquid composition alone) and when the enzyme is used in a PVA/PS (i.e, polyvinylalcohol polystyrene) capsule as described in U.S. Ser. No. 08/037,053 hereby incorporated by reference into the subject application. The results are set forth in the Table below:

| | % Residual Activity | | | |
|---|---|---|---|---|
| Days | Liquid* | PVA/PS | Slurry** | Capsule ┼ |
| 0 | 100 | 100 | 100 | 100 |
| 2 | 0 | 0 | 44 | 95 |
| 6 | — | — | <5 | 68 |

*Liquid - Savinase 16.0 L
**Slurry - Savinase 16 SL/SR
┼Capsule
Stabilities studies conducted at 37° C. using a duotropic HDL of Table I containing SBPB (4,4'-sulfonylbisperoxybenzoic acid) having 1000 ppm active oxygen and enzymes having 18 GU/mg activity As can be seen from the table above, the stability of the enzyme in the composition alone or in the composition encapsuled by polymer (PVA/PS) but no oil or slurry, was almost zero after 2 days. With slurry alone, some improvement was seen. However the results using the combination of slurry encapsulation are far superior to the slurry alone.

The example clearly shows that the use of both an oil or slurry layer and encapsulation is superior to either one alone.

EXAMPLE 2

In order to determine the stability of enzyme used in compositions comprising bleach peracids when the enzyme is protected by the capsules of the invention, the stability of Savinase was tested in composition comprising one of two peracids, N,N'-Di(4-Percarboxybenzoyl)piperazine (PCBPIP), or N,N'-terephthaloyl-di (6-aminopercarboxycaproic acid) (TPCAP). While the presence of peracids would normally destroy all enzyme activity almost immediately, the following results were seen using the capsules of the invention.

| EXAMPLE 2 | |
|---|---|
| Time (Days) | PCBPIP % Residual Enzyme Activity |
| 0 | 100 |
| 2 | 99 |
| 6 | 117 |
| 13 | 77 |
| 17 | 57 |
| 20 | 67 |
| 31 | 38 |
| Time (Days) | TPCAP % Residual Enzyme Activity |
| 0 | 100 |
| 4 | 68 |
| 7 | 58 |
| 16 | 65 |
| 23 | 44 |
| 42 | 32 |

Capsule composition is that of preparative example (Table 1 above). Stability studies conducted at 37° C. in the same HDL as Table 1 except that it contained one of the two peracids dosed at 1000 ppm of active oxygen instead of SBPB The efficiency of the capsules can be clearly seen.

Again this example shows efficiency of encapsulated slurry.

EXAMPLE 3

In order to make sure that enzyme is released into wash from the capsules, applicants tested percent activity released over time and the following results were observed.

| EXAMPLE 3 | |
|---|---|
| Time (Minutes) | % Activity Released |
| 0 | 14.6 |
| 5 | 75.9 |
| 10 | 100.00 |
| 15 | 96.5 |

Conditions: 40° C., 120 ppm $Ca^{+2}$
Capsules were placed in the liquid composition described above (Table 1)

As can be clearly seen release from capsules is more than 70% at the first 5 minutes wash and is complete after 10 minutes.

The example again shows that the encapsulated oils release well.

EXAMPLE 4AND 5 AND COMPARATIVES A AND B

In order to show that some hydrophobic oils were superior to others when used in the capsule, protease was tested in various oils. It should be noted that each of the capsules were prepared by the matrix method described in the preparatory example. Results for yield and percent residual activity are set forth below.

More specifically, slurry compositions were made comprising concentrated savinase and an oil as follows:

| | Composition | Savinase Activity (GU/g) of Slurry |
|---|---|---|
| Slurry Composition 1 | 70% Rodosil LV461 (Silicone antifoam 10,000 cps); and 30% Savinase concentrate | $1.6 \times 10^7$ |
| Slurry Composition 2 (Comparative) | 70% Silicone oil 30% Savinase concentrate | $2.4 \times 10^7$ |
| Slurry Composition 3 (Comparative) | 60% Mineral oil 40% Savinase concentrate | $2.7 \times 10^7$ |
| Slurry Composition 4 | 36% Mineral oil 24% Petrolatum 40% Savinase concentrate | $2.7 \times 10^7$ |

Compositions were then formed from the slurry compositions comprising 66.6% by weight of the slurry composition and 33.4% by weight ASE 95 solution (1.5%).

Finally, these compositions were then made into capsules using the matrix encapsulation method. Capsules formed from slurry compositions I and 4 were designated as Examples 4, 5 and capsules formed from slurry compositions 2 & 3 were designated as comparative examples A&B.

Applicants then tested (1) the Savinase activity inside the capsule after capsule was in the composition of Table 1 additionally containing SBPB peracid bleach (4,4-sulfonybisperoxybenzoic acid) to determine what % of the original activity (as set forth in the table above) this represented and (2) the % residual activity of enzyme for each capsule when measured after 3 days at 37° C. Results are set forth below.

| | Savinase Activity in Capsule | % of Original Activity this Represents | % Residual Activity After 3 Days at 37° C. |
|---|---|---|---|
| Example 4 | $4.5 \times 10^6$ | 28% | 50% |
| Comparative A | $2.7 \times 10^5$ | 1.2% | 0% |
| Comparative B | $1.2 \times 10^5$ | 0.4% | 3% |
| Example 5 | $1.0 \times 10^6$ | 3.7% | 25% |

As can be clearly seen, Examples 4 and 5, which represent oil or oils meeting all three criteria of the invention, retained a high % of original activity (28% and 3.7%) relative to the Comparative examples (1.2% at 0.4%) which oils did not meet all criteria. In addition, the residual activity after three days was also clearly superior.

The silicone oil (Comparative A) and mineral oil (Comparative B) showed poor trapping efficiency and also lost enzyme activity rapidly in the bleach containing liquid. Addition of petrolatum to mineral oil (Example 5) can enhance the oil trapping efficiency during capsule preparation and can also dramatically enhance the performance of the capsule. The same result was observed by using Rhodisil LV461, which is a silicone oil containing hydrophobically modified silica.

The examples shows the oil composition is not only important to the trapping efficiency of enzyme during preparation of the capsule, but is also critical in enhancing enzyme stability when enzyme is used in a peracid-containing heavy duty liquid detergent.

While not wishing to be bound by theory it is believed that those oils having the capability to stop the enzyme from dispersing or diffusing out of the oil and the capability to minimize the penetration of harsh detergent ingredients into the capsule during capsule preparation and storage are the ones which show greatest yield and residual activity over time.

EXAMPLES 6–9 AND COMPARATIVE EXAMPLES C, D, & E

The following examples are used to show the preparation of the capsule and the effectiveness of the capsules in protecting actives/enzymes relative to the closest prior art.

Preparation of Capsule Compositions

Oil Slurries

Enzyme dispersions were first prepared by dispersing Savinase enzyme particles (protease) in various oils using Dispermate (UMA-GETZMANN) at 2000 rpm for 10 minutes: The following seven (7) oil dispersions were prepared:

| | Oil (% by Wt.) | Savinase Particle (% by wt.) |
|---|---|---|
| Comparative C* | 92% SAG1000 Silicone Antifoam (Union Carbide) | 8% |
| 6 | 92% Rhodosil LV461 Silicone Antifoam (Rhone-Poulenc) | 8% |
| Comparative D | 92% Silicone Oil 10,000 (Union Carbide) | 8% |
| Comparative E | 95% Mineral Oil (Fisher) | 8% |
| 7 | 88.7% Mineral Oil (Fisher)/3.7% Carbosil TS720 | 8% |
| 8 | 92% Tro-Grees (Penreco) | 8% |
| 9 | 92% Snow White Petrolatum (Penreco) | 8% |

*This was considered to be a comparative because the enzyme particles phase separated out of the oil during storage.

Capsules

Core shell Savinase enzyme capsules (as distinct from the matrix capsule preparation) were then prepared by encapsulating the enzyme dispersions noted above with a polymer solution containing polyvinyl alcohol (Airvol 540) and Acrysol ASE-60 (which is an alkali-soluble emulsion thickener from Rohm & Haas) using a concentric triple nozzle.

Specifically, the enzyme-in-oil dispersion was fed through the inside orifice, the polymer aqueous solution was fed through the middle orifice and a compressed air was passed through the outside orifice to make enzyme capsules of 600 to 800 micrometers. These capsules were hardened and stored in a salt solution containing 15 weight percent of sodium sulfate and 2 weight percent of sodium borax with a pH in a range of 6 to 7. The following capsule examples 6-9 and Comparative Examples C-E were thus prepared from the seven dispersions.

| | Composition of Capsule |
|---|---|
| Capsule of Comparative C | 1 part enzyme dispersion 1 (silicone antifoam) and 6.7 parts polymer solution A* |
| Capsule 6 | 1 part enzyme dispersion 2 (silicone antifoam) and 6 parts polymer solution A* |
| Capsule of Comparative D | 1 part enzyme dispersion 3 (silicone oil 10,000) and 6.7 parts polymer solution A* |
| Capsule of Comparative E | 1 part enzyme dispersion 4 (mineral oil) and 6 parts polymer solution B** |
| Capsule 7 | 1 part enzyme dispersion 5 (mineral oil and Carbosil) and 6 parts polymer solution B** |
| Capsule 8 | 1 part enzyme dispersion 6 (Tro-Grees 5) and 6 parts polymer solution B** |
| Capsule 9 | 1 part enzyme dispersion 7 (Petrolatum) and 6 parts polymer solution B** |

*Polymer Solution A contains 2.7% Airvol 540 PVA (Air product) and 1.3% Acrysol ASE-60 (Rohm & Haas).
**Polymer Solution B contains 2.3% Airvol 540 and 1.2% Acrysol ASE-60.

Compositions

Enzyme capsules 6-9 and capsules comparative C-E were then formulated into a liquid detergent containing 95.4 wt. % of a stable liquid detergent formula having the following composition.

| BASE FORMULA OF LIQUID DETERGENT | |
|---|---|
| Water | 24.8 |
| Sorbdol (70%) | 15.8 |
| Glycerol | 4.76 |
| Sodium Borate $10H_2O$ | 4.76 |
| Sodium Citrate $2H_2O$ | 9.52 |
| Narlex DC-1 (ex. National Starch & Chem.) | 3.0 |
| 50% NaOH | 5.43 |
| DB100 (Dow Chem.) (Antifoam) | 0.1 |
| Alkyl Benzene Sulfonic Acid | 21.83 |
| Neodol 25-9 (Nonionic) | 10.0 |
| Total | 100.00 |

and additionally contain 4.6 wt. % of stable peracid N,N'-Terephthaloyl di(6-aminopercarboxycaproic acid) (TPCAP) which was prepared as described in WO Patent 9,014,336.

The enzyme capsules were incorporated into the above-identified formulation to give 16,000 GU enzyme activity per gram of the formulated liquid detergent. These formulated samples were stored at 37° C. and the residual Savinase activity of these stored samples was determined and given in the left column of the Table shown below:

TABLE

Residual Enzyme Activity of Examples

| | % Residual Enzyme Activity (when encapsulated) | % Residual Enzyme Activity (when not encapsulated) |
|---|---|---|
| Comparative C | 45% after 6 days 28% after 20 days | 0% after 3 days |
| Example 6 | 22.4% after 14 days | 0% after 3 days |
| Comparative D | 35% after 6 days 18% after 20 days | 0% after 3 days |
| Comparative E | 38.3% after 14 days | 0% after 3 days |
| Example 7 | 61.7% after 14 days | 0% after 3 days |
| Example 8 | 76.8% after 14 days | 0% after 3 days |
| Example 9 | 76.6% after 14 days | 7% after 6 days |

In order to show that the capsules of the invention function by retaining enzyme activity while the enzyme slurry alone (i.e., nonencapsulated) cannot and does not retain the same enzyme levels, applicants prepared the same Examples 6–9 and comparative examples C-E, but did not encapsulate (i.e., right hand column of Table). The slurry only examples correspond to the system used in U.S. Pat. No. 4,906,396 to Falholz.

The slurry-only examples were prepared by stirring the prepared enzyme-in-oil dispersion into the same liquid detergent as used in the capsule examples which contained 4.6% TPCAP peracid and was stored at 37° C. As noted, the residual Savinase enzyme activity of these slurry-only examples was shown in the right column of the Table.

The enzyme stability data summarized in the Table clearly shows that the protected enzyme system as claimed by U.S. Pat. No. 4,906,396 did not provide a protection to the enzyme in the bleach-containing liquid detergent. Almost 0% of enzyme activity remained for all of the slurry-only examples after being stored at 37° C. for less than 1 week. Depending on the oil used in the capsule composition of this invention, 22 to 78% of enzyme activity still remained after being stored in this bleach-containing liquid for 2 weeks.

EXAMPLE 10—PERFORMANCE

The performance of 3 Savinase enzyme capsules (Examples 6, 8 and 9) of this invention was compared with a liquid Savinase in the wash for stain removal. A test doth (AS10 Cloth, ex. Center for Test Material) stained with casein, pigments and oils was used. The performance of these Savinase capsules containing liquid detergent and the control sample containing the liquid Savinase was summarized in Table 2 below. Delta Delta R values, which indicates the whiteness of the washed cloth, show the capsule of this invention released the encapsulated enzyme and performed the same as the free Savinase. Table 2 is set forth below:

TABLE 2

ENZYME RELEASE IN WASH

| Enzyme Sample | Delta Delta R |
|---|---|
| Control (Savinase Liquid) | 11.0 |
| Capsule of Example 6 | 7.9 |
| Capsule of Example 8 | 9.3 |
| Capsule of Example 9 | 10.5 |

EXAMPLE 11

Another example using encapsulated lipase is described below:

A Lipolase enzyme particle was prepared by spray drying a mixture of 30 wt. % Lipolase 100L (Novo) and 70 wt. % of Airvol 1603/polystyrene latex to give an enzyme particle with $210\times10^3$ LU/g Lipolase activity. A Lipolase-in-oil dispersion was prepared by dispersing 25 wt. % of this Lipolase particle to 75 wt. % of Rhodosil LV461 Silicone antifoam (ex. Rhone-Poulenc). One part of the Lipolase-in-oil dispersion was mixed with 3 parts of Acrysol ASE-95 solution (1.8 wt. %, pH 7.5–8.0) with an overhead stirrer to make an enzyme-in-oil-in-water emulsion. A matrix enzyme capsule was prepared by adding the Lipolase-in-oil-in-water emulsion dropwise to an acid bath containing 98% water and 2% concentrate $H_2SO_4$. The capsule has a particle size about 1,000 micrometers and $19\times10^3$ LU/g Lipolase activity. A liquid detergent containing 88 wt. % of the base liquid detergent of Examples 6–9, 10 wt. % benzoyl peroxide and 2% of Lipolase capsule was formulated and stored at 37° C. A comparative example containing the nonencapsulated Lipolase 100L was also formulated with the same liquid detergent containing 10 wt. % benzoyl peroxide and stored at 37° C. for I week is: 0% for the comparative example and 58% for the Lipolase capsule of this invention.

EXAMPLES 12–14

The following examples were used to show the preparation and the effectiveness of the capsules in protecting PAP in a heavy duty liquid.

Preparationof Capsule Components

PAP-in-Oil Dispersions:

PAP (phthalamidoperoxycaproic acid) dispersions were prepared by mixing PAP crystal in the various oils meeting the criteria set forth in the invention using Dispermat (F1, VMA-Getzmann) at 2000 rpm for 10 minutes. Three dispersions were prepared, as shown in the Table below:

TABLE

PAP-in-Oil Dispersions

| No | Oil Type | Oil wt. % | PAP Crystal (wt %) |
|---|---|---|---|
| 1 | Silicone Antifoam (LV461, Rhodosil) | 80 | 20 |
| 2 | Tro-Grees (Spray S, Penreco) | 80 | 20 |
| 3 | Petrolatum (Snow White, Penreco) | 80 | 20 |

Each of these oils has the characteristics defining the oils of the invention (i.e., retains greater than 80% crystals, preferably greater than 90% crystal after capsule preparation, suspends active with less than 10% phase separation under defined conditions and releases per defined conditions).

Capsules

Core-shell PAP capsules were then prepared by encapsulating the PAP dispersions noted above with a polymer solution containing 3.3 wt. % of polyvinyl alcohol (Airvol 540, Air Products) and 1.7 wt. % of alkaline soluble polymer (ASE-60, Rhom & Haas) using a concentric triple nozzle.

Specifically, the PAP-in-oil dispersion, polymer solution, and compressed air were simultaneously fed to the nozzle tip through the central, middle, and outer orifices, respectively. Three PAP capsules of 600–800 pm were prepared from the three dispersions, as shown in the Table below:

TABLE 2

| PAP Core-Shell Capsules | |
|---|---|
| Example | Capsule Composition |
| Capsule 12 | 1 part of PAP dispersion 1 (Silicone Antifoam) and 5 parts of polymer solution |
| Capsule 13 | 1 part of PAP dispersion 2 (Tro-Grees) and 5 parts of polymer solution |
| Capsule 14 | 1 part of PAP dispersion 3 (Petrolatum) and 5 parts of polymer solution |

Composition

PAP capsules 1-3 were then formulated into a liquid detergent having the following composition:

TABLE 3

| Basic Formula of Liquid Detergent | |
|---|---|
| Ingredients | Wt. % |
| Sorbitol (70%) | 15.8 |
| Glycerol | 4.8 |
| Sodium Borate 10 $H_2O$ | 4.8 |
| Sodium Citrate 2 $H_2O$ | 9.5 |
| Narlex DC-1 (33%) | 2.9 |
| Sodium Hydroxide (50%) | 5.5 |
| DB 100 (Silicone antifoam) | 0.1 |
| BDA (Alkyl benzene sulphonic acid) | 21.8 |
| Neodol 25-9 (Nonionic surfactant having average alkoxylation of about 9 | 10.0 |
| Water | 24.9 |

PAP capsule was incorporated into the formulation to give 4000 ppm of active oxygen per gram of the formulated liquid detergent. These formulated samples were stored at 37° C. and the residual PAP activity of these stored samples was determined and given in the Table below.

TABLE 4

| Residual PAP Activity of Examples 12–14 | | |
|---|---|---|
| Example No. | Storage Time (days) | Residual Activity |
| PAP Crystal | 2 | 50 |
| | 3 | 25 |
| Capsule 12 | 4 | 50 |
| | 6 | 25 |
| Capsule 13 | 8 | 50 |
| | 15 | 30 |
| Capsule 14 | 15 | 75 |
| | 30 | 52 |

The stability results show the stability of PAP in a liquid detergent can be dramatically enhanced by protecting PAP in the capsule of this invention.

EXAMPLE 15

The following examples are used to show the preparation and the effectiveness of the capsules in protecting manganese bleach catalyst [MnMeTACN,di(N,N',N"-trimethyl- 1,4,7,-triazacy clononane )-tri(Mu-oxo )-dimanganese (IV)di(hexafiuorophosphate-monohydrate)] in a heavy duty liquid detergent.

Preparation of Capsule Components

Catalyst-in-Oil Dispersions:

Catalyst dispersions were prepared by mixing the manganese bleach catalyst in various oils using Dispermat (FI, VMA-Getzmann) at 2000 rpm for 10 minutes. The dispersion contained 81% of Tro-Grees, 9% of Petrolatum, and 10% of manganese bleach catalyst.

Capsules:

The core-shell bleach catalyst capsule was then prepared by encapsulating the bleach catalyst dispersions same as Examples 12–14 with a polymer solution containing 3.3 wt. % of polyvinyl alcohol (Airvol 540, Air Products) and 1.7 wt. % of alkaline soluble polymer (ASE-60, Rhom & Haas) using a concentric triple nozzle.

Specifically, the catalyst-in-oil dispersion polymer solution and compressed air were simultaneously fed to the nozzle tip through the central, middle and outer orifices, respectively.

| Compositions of Bleach Catalyst Capsules | |
|---|---|
| Example No. | Capsule Composition |
| 15 | 1 part of magnesium bleach catalyst dispersion 1 (mixture of Petrolatum and Tro-Grees) and 8 parts of polymer solution |

The capsules were then formulated into a liquid detergent having the following composition:

TABLE 3

| Basic Formula of Liquid Detergent | |
|---|---|
| Ingredients | Wt. % |
| Sodium Metaborate | 1.50 |
| Sodium Perborate | 10.00 |
| Sodium Citrate | 10.00 |
| Narlex DC-1 (33%) | 4.50 |
| BDA (97%) | 20.10 |
| Neodol 25-9 | 8.60 |
| Antifoam | 0.25 |
| Water | 35.0 |
| Sodium Hydroxide (50%) | adjust pH to 10 |

The capsule was incorporated into the formulation to give 0.2% of active bleach catalyst in the formulated liquid detergent. The formulated samples were stored at 37° C. and 22° C. the residual catalyst activity of these stored samples was determined and given in the Table below.

TABLE 4

| Residual Bleach Catalyst Activity of Examples 1-3 | | | |
|---|---|---|---|
| Example No. | Storage Temperature (°C.) | Storage Time (days) | Residual Activity (%) |
| Bleach Catalyst | 37 | 1 | 0% |
| (Comparative) | 22 | 1 | 0% |
| Bleach Catalyst | 37 | 5 | 95% |
| Capsule | 22 | 5 | 98% |
| (Example 15) | 37 | 45 | 52% |
| | 22 | 45 | 72% |

We claim:

1. A capsule composition for use in an aqueous liquid cleaning composition comprising:

(a) an active which is degraded by components in said aqueous liquid composition;

(b) an oil dispersion containing said active, wherein said oil is defined: (1) by its ability to retain greater than 80% active in oil after an hour when the dispersion of active in oil is added to an aqueous solution containing 0.5 wt. % sodium lauryl sulfate; (2) the ability to suspend said active with less than 10% phase separation when stored at 37° C. for 1 week; and (3) by the ability to release more than 50% active after 5 minutes of a wash cycle when measured at 40° C.; and (c) a polymer shell surrounding the oil dispersion of (b), wherein said polymer shell is a water soluble polymer or water dispersible polymers selected from at least one of the groups consisting of polyvinyl alcohol, a polyacrylamide, polyvinyl pyrrolidone, carrageenan, guar gum, xanthan gum, cellulose and protein;

wherein the active of (b)(i) is not modified with a hydrophobic matrix polymer.

2. A capsule according to claim 1, wherein said active is a hydrophilic active.

3. A capsule according to claim 2, wherein said active is selected from the group consisting of enzymes, peracid bleach, bleach catalyst, bleach activators and optical brighteners.

4. A capsule according to claim 3, wherein said active is an enzyme or enzymes selected from the group consisting of proteases, lipases, amylases, cellulases, and oxidases.

5. A capsule according to claim 3, wherein said bleach activator is selected from the group consisting of tetraacetylethylenediamine, tetraacetyglycoludl, glucosepentaacetate, xylose tetraacetate, sodium benzoyloxybenzene sulfonate and choline sulfophenyl carbonate.

6. A capsule according to claim 3, wherein said peracid bleach is PAP.

7. A capsule according to claim 3, wherein said bleach catalyst is a manganese catalyst or a sulfonomine or suifonomine derivative catalyst.

8. A capsule according to claim 1, wherein said oil is selected from at least one of the groups consisting of petrolatum, hydrocarbon oil modified with hydrophobic silica, silicone oil modified with hydrophobic silica and fat.

* * * * *